(12) United States Patent
Shimizu et al.

(10) Patent No.: US 7,078,568 B2
(45) Date of Patent: Jul. 18, 2006

(54) PHOSPHINE COMPOUNDS, TRANSITION METAL COMPLEXES WITH THE COMPOUNDS CONTAINED AS LIGANDS THEREIN, AND ASYMMETRIC SYNTHESIS CATALYSTS CONTAINING THE COMPLEXES

(75) Inventors: Hideo Shimizu, Hiratsuka (JP); Takao Saito, Hiratsuka (JP); Izuru Nagasaki, Hiratsuka (JP)

(73) Assignee: Takasago International Corporation, Hiratsuka (JP)

( * ) Notice: Subject to any disclaimer, the term of this patent is extended or adjusted under 35 U.S.C. 154(b) by 0 days.

(21) Appl. No.: 11/206,068

(22) Filed: Aug. 18, 2005

(65) Prior Publication Data

US 2005/0288531 A1  Dec. 29, 2005

Related U.S. Application Data

(62) Division of application No. 10/701,430, filed on Nov. 6, 2003, now Pat. No. 6,987,202.

(30) Foreign Application Priority Data

Nov. 12, 2002  (JP) ............................. 2002-327889

(51) Int. Cl.
C07F 9/02 (2006.01)
(52) U.S. Cl. .......................................... 568/12; 568/17
(58) Field of Classification Search .................. 568/12, 568/17
See application file for complete search history.

(56) References Cited

U.S. PATENT DOCUMENTS

| | | | | |
|---|---|---|---|---|
| 5,171,892 A | 12/1992 | Burk | ............................. | 568/12 |
| 5,516,944 A | 5/1996 | Broger et al. | .................. | 568/13 |

FOREIGN PATENT DOCUMENTS

| | | |
|---|---|---|
| JP | 6-508848 | 10/1994 |
| JP | 7-149777 | 6/1995 |
| JP | 2002-527444 | 8/2002 |
| JP | 2002-527445 | 8/2002 |
| WO | 93/01199 | 2/1993 |
| WO | 00/21970 | 4/2000 |
| WO | 00/21971 | 4/2000 |

OTHER PUBLICATIONS

Castro, et al., "Unexpected Roles of Guest Polarizability and Maximum Hardness, and a Host of Solvation in Supramolecular Inclusion Complexes: A Dual Theoretical and Experimental Study", J. Am. Chem. Soc., 1996, 118, 10257-10268.

Koh, J.H., et al., "Disparate Roles of Chiral Ligands and Molecularly Imprinted Cavities in Asymmetric Catalysis and Chiral Poisoning", Organometallics, 2002, 21, 7-9.

Ogawara, M., et al., "Synthesis and Characaterization of a Novel Chiral Phospole and Its Derivatives", Organometallics, 2001, 20, 1014-1019.

Brunet, J-J., et al., "Catalytic Asymmetric hydrogenation using rhodium complexes of DIPPOP, a chiral ligand bearing two phospholyl moieties", Journal of Molecular Catalysis, 1992, 72, L21-L25, M2852.

Noyori, R., "Homogeneous Asymmetric Hydrogenation", Asymmetric Catalysis In Organic Synthesis, 1994, Chapter 2, 16-94.

Saito, T., et al., "New Chiral Diphosphine Ligands Designed to Have a Narrow Dihedral Angle in the Biaryl Backbone", Adv. Synth. Catal., 2001, 343, 264-267, XP-002253903.

*Primary Examiner*—Sikarl A. Witherspoon
(74) *Attorney, Agent, or Firm*—Oblon, Spivak, McClelland, Maier & Neustadt, P.C.

(57) ABSTRACT

Phosphine compounds represented by the following formula (1):

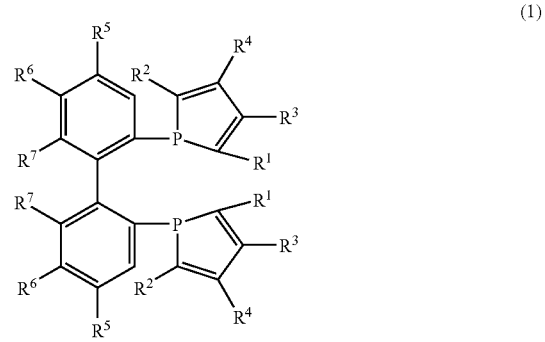

wherein $R^1$, $R^2$, $R^3$, $R^4$, $R^5$, $R^6$ and $R^7$ represent substituents, and asymmetric synthesis catalysts containing transition metal phosphine complexes with the compounds contained as ligands therein.

The novel phosphine compounds according to the present invention are useful especially as ligands in transition metal complexes. The transition metal phosphine complexes are useful as catalysts for asymmetric synthetic reactions. The novel phosphine compounds useful as ligands can be prepared by a relatively economical preparation process. Further, use of these catalysts can afford hydrogenated products with high optically purity and is also extremely useful from the industrial standpoint.

18 Claims, No Drawings

PHOSPHINE COMPOUNDS, TRANSITION METAL COMPLEXES WITH THE COMPOUNDS CONTAINED AS LIGANDS THEREIN, AND ASYMMETRIC SYNTHESIS CATALYSTS CONTAINING THE COMPLEXES

This application is a Divisional application of U.S. application Ser. No. 10/701,430, filed on Nov. 6, 2003 now U.S. Pat. No. 6,987,202.

TECHNICAL FIELD

This invention relates to novel phosphine compounds, production intermediates thereof, transition metal complexes with the phosphine compounds contained as ligands therein, and transition metal complex catalysts useful as catalysts for various asymmetric synthetic reactions.

BACKGROUND ART

Numerous reports have been published to date on transition metal complex catalysts usable in catalytic asymmetric syntheses such as asymmetric hydrogenation reactions, asymmetric hydrosilylation reactions, asymmetric hydroformylation reactions and asymmetric isomerization reactions. Among these, transition metal complexes of ruthenium, iridium, rhodium, palladium, nickel or the like, which contain optically active phosphines as ligands, have been reported to possess excellent performance as catalysts for asymmetric synthetic reactions, and some of them are already used in the industrial application [Asymmetric Catalysis in Organic Synthesis, Ed., R. Noyori, Wiley & Sons (1994)].

Phosphole compounds, meanwhile, have been extensively studied for many years with respect to their syntheses and physical properties, but there are still few instances confirming the fact that phosphole compounds were applied to syntheses or asymmetric reactions of optically active substances.

In recent years, some optically active diphosphine ligands each containing one or more phosphole moieties have been reported, and have also been applied to asymmetric hydrogenation reactions (J. Mol. Cat., 72, 21–25, 1992; Organometallics, 20, 1014–1019, 2001).

Among the compounds reported so far are chiral transition metal complexes of chiral bis(phosphorane) obtained using chiral 1,4-diol cyclic sulfate esters as precursors (JP 6-508848 A), diphosphine derivatives (JP 7-149777 A), diphosphole derivatives (JP 2002-527444 A), isophosphindolinic acids (JP 2002-527445 A), etc.

However, these optically active diphosphine ligands, each of which contains one or more phosphole moieties, are not yet free from the problems associated with the industrial viewpoint, because their syntheses are all required to go through cleavage by metallic lithium of carbon-phosphorus bonds in the corresponding 1-phenylphosphole compounds.

Moreover, these ligands require improvements of catalysts if they are not sufficient in selectivity (chemical selectively, enantio-selectivity) and catalytic activities, depending on this reaction targets or their reaction substrates.

DISCLOSURE OF THE INVENTION

An object of the present invention is to provide a novel phosphine compound and also, an asymmetric synthesis catalyst which contains a transition metal phosphine complex with the phosphine compound contained as a ligand therein and which has excellent performance in chemical selectivity, enantio-selectivity, catalytic activities and the like as a catalyst for asymmetric synthetic reactions, especially for asymmetric hydrogenation reactions.

To solve the above-described problems, the present inventors have carried out extensive researches. As a result, it has been found that transition metal catalysts containing primary phosphines of a particular construction, especially phosphine compounds derived from axially asymmetric, pave the way to solve the overall problems left to asymmetric hydrogenation reactions. Thus, the present invention was accomplished.

In one aspect of the present invention, there is thus provided a phosphine compound represented by the following formula (1):

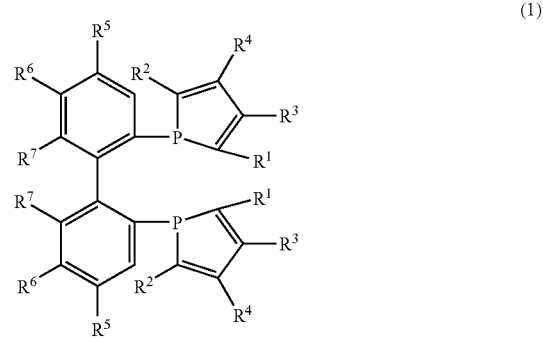

(1)

In the above formula (1), $R^1$ and $R^2$ each independently represents a hydrogen atom, a substituted or unsubstituted $C_{1-10}$ alkyl group, a substituted or unsubstituted $C_{1-10}$ alkoxy group, a substituted or unsubstituted $C_{2-10}$ alkenyl group, a substituted or unsubstituted di($C_{1-5}$ alkyl)amino group, a substituted or unsubstituted, 5- to 8-membered cyclic amino group, a substituted or unsubstituted, 5- to 8-membered alicyclic group, a substituted or unsubstituted aryl group, a substituted or unsubstituted aralkyl group, a substituted or unsubstituted heterocyclic group, a trisubstituted silyl group or a halogen atom. $R^3$, $R^4$, $R^5$ and $R^6$ each independently represents a hydrogen atom, a $C_{1-5}$ alkyl group, a $C_{1-5}$ alkoxy group, a di($C_{1-5}$ alkyl)amino group, a 5- to 8-membered cyclic amino group or a halogen atom. $R^7$ represents a $C_{1-5}$ alkyl group, a $C_{1-5}$ alkoxy group, a di($C_{1-5}$ alkyl) amino group, a 5- to 8-membered cyclic amino group or a halogen atom. $R^3$ and $R^4$, $R^5$ and $R^6$, and $R^6$ and $R^7$ may each be fused together to form a fused benzene ring, a fused, substituted benzene ring, a trimethylene group, a tetramethylene group, a pentamethylene group, a methylenedioxy group, an ethylenedioxy group or a trimethylenedioxy group.

In other aspects of the present invention, there are also provided a transition metal phosphine complex with the phosphine compound, which is represented by the formula (1), contained as a ligand therein; and also an asymmetric synthesis catalyst containing the transition metal phosphine complex.

In a still further aspect of the present invention, there is also provided a primary phosphine compound represented by the following formula (2):

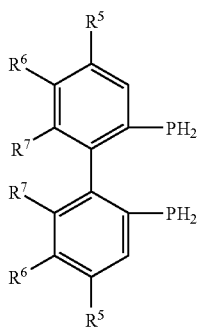

(2)

wherein $R^5$, $R^6$ and $R^7$ have the same meanings as defined above.

Incidentally, an optically active, primary phosphine having the biaryl skeleton is referred to in JP 6-508848 A, which however discloses nothing more than a mere chemical structure and makes no mention whatsoever about its production process, to say nothing about a description on an optically active substance.

The novel phosphine compound according to the present invention is useful especially as a ligand in a transition metal complex. The transition metal phosphine complex, on the other hand, is useful as a catalyst for asymmetric synthetic reactions. The novel phosphine compound useful as a ligand can be prepared by a relatively economical preparation process. Further, use of this catalyst makes it possible to obtain an asymmetric hydride of high optical purity with good yield so that this catalyst is also extremely useful from the industrial standpoint.

BEST MODES FOR CARRYING OUT THE INVENTION

The present invention will hereinafter be described in detail.

In the phosphine compound of the present invention represented by the formula (1), specific examples of the $C_{1-10}$ alkyl group represented by $R^1$ or $R^2$ can include methyl, ethyl, n-propyl, isopropyl, n-butyl, isobutyl, sec-butyl, tert-butyl, pentyl, hexyl, heptyl, octyl, nonyl, and decyl. These alkyl groups may each contain, as substituent (s), 1 to 4 functional groups which are inert to asymmetric synthetic reactions. Illustrative of the substituent (s) are hydroxyl; $C_{1-4}$ alkoxy groups such as methoxy, ethoxy, n-propoxy, isopropoxy, n-butoxy, isobutoxy, sec-butoxy and tert-butoxy; and halogen atoms such as fluorine, chlorine, bromine and iodine.

Specific examples of the $C_{1-10}$ alkoxy group represented by $R^1$ or $R^2$ can include methoxy, ethoxy, n-propoxy, isopropoxy, n-butoxy, isobutoxy, sec-butoxy, tert-butoxy, pentoxy, hexyloxy, heptyloxy, octyloxy, nonyloxy and decyloxy. These alkoxy groups may each contain, as substituent(s), 1 to 4 functional groups which are inert to asymmetric synthetic reactions. Illustrative of the substituent(s) are $C_{1-4}$ alkyl groups such as methyl, ethyl, n-propyl, isopropyl, n-butyl, isobutyl, sec-butyl and tert-butyl; hydroxyl; $C_{1-4}$ alkoxy groups such as methoxy, ethoxy, n-propoxy, isopropoxy, n-butoxy, isobutoxy, sec-butoxy and tert-butoxy; and halogen atoms such as fluorine, chlorine, bromine and iodine.

Specific examples of the $C_{2-10}$ alkenyl group represented by $R^1$ or $R^2$ can include vinyl, allyl, 1-propenyl, isopropenyl, 1-butenyl, 2-butenyl, 2-methylallyl, pentenyl, hexenyl, heptenyl, octenyl, nonenyl, and decenyl. These alkenyl groups may each contain, as substituent (s), 1 to 4 functional groups which are inert to asymmetric synthetic reactions. Illustrative of the substituent(s) are $C_{1-4}$ alkyl groups such as methyl, ethyl, n-propyl, isopropyl, n-butyl, isobutyl, sec-butyl and tert-butyl; hydroxyl; $C_{1-4}$ alkoxy groups such as methoxy, ethoxy, n-propoxy, isopropoxy, n-butoxy, isobutoxy, sec-butoxy and tert-butoxy; phenyl; and halogen atoms such as fluorine, chlorine, bromine and iodine.

Specific examples of the di($C_{1-5}$ alkyl)amino group represented by $R^1$ or $R^2$ can include dimethylamino, diethylamino, di(n-propyl)amino, diisopropylamino, di(n-butyl)amino, diisobutylamino, di(sec-butyl)amino, di(tert-butyl)amino, and dipentyl amino. These di($C_{1-5}$ alkyl)amino groups may each contain, as substituent(s), 1 to 4 functional groups which are inert to asymmetric synthetic reactions. Illustrative of the substituent(s) are hydroxyl; $C_{1-4}$ alkoxy groups such as methoxy, ethoxy, n-propoxy, isopropoxy, n-butoxy, isobutoxy, sec-butoxy and tert-butoxy; and halogen atoms such as fluorine, chlorine, bromine and iodine.

Specific examples of the 5- to 8-membered, cyclic amino group represented by $R^1$ or $R^2$ can include pyrrolidino and piperidino. These cyclic amino groups may each contain, as substituent(s), 1 to 4 functional groups which are inert to asymmetric synthetic reactions. Illustrative of the substituent(s) are $C_{1-4}$ alkoxy groups and halogen atoms.

Specific examples of the substituted or unsubstituted, 5- to 8-membered alicyclic group represented by $R^1$ or $R^2$ can include cyclopentyl, cyclohexyl, cycloheptyl and cyclooctyl. Illustrative of substituents on these 5- to 8-membered alicyclic groups are $C_{1-4}$ alkyl groups, a hydroxyl group, $C_{1-4}$ alkoxy groups and halogn atoms. The alicyclic groups may each contain 1 to 4 of these substituents. Specific examples of the substituent(s) are $C_{1-4}$ alkyl groups such as methyl, ethyl, n-propyl, isopropyl, n-butyl, isobutyl, sec-butyl and tert-butyl; hydroxyl; $C_{1-4}$ alkoxy groups such as methoxy, ethoxy, n-propoxy, isopropoxy, n-butoxy, isobutoxy, sec-butoxy and tert-butoxy; and halogen atoms such as fluorine, chlorine, bromine and iodine.

Specific examples of the substituted or unsubstituted, aryl group represented by $R^1$ or $R^2$ can include $C_{6-10}$ aryl groups such as phenyl, naphthalen-1-yl, and naphthalen-2-yl. Illustrative of substituents on the aryl groups are $C_{1-4}$ alkyl groups, hydroxyl group, $C_{1-4}$ alkoxy groups, and halogen groups. The aryl groups may each contain 1 to 5 substituents selected from these substituents. Specific examples of the substituents can include $C_{1-4}$ alkyl groups such as methyl, ethyl, n-propyl, isopropyl, n-butyl, isobutyl, sec-butyl and tert-butyl; hydroxyl; $C_{1-4}$ alkoxy groups such as methoxy, ethoxy, n-propoxy, isopropoxy, n-butoxy, isobutoxy, sec-butoxy and tert-butoxy; and halogen atoms such as fluorine, chlorine, bromine and iodine.

Specific examples of the substituted or unsubstituted, aralkyl group represented by $R^1$ or $R^2$ can include aralkyl groups each having 7 to 15 carbon atoms in total, such as benzyl, α-phenethyl, β-phenethyl, α-phenylpropyl, β-phenylpropyl, γ-phenylpropyl, and naphthylmethyl. Illustrative of substituents on these aralkyl groups are $C_{1-4}$ alkyl groups, hydroxyl group, $C_{1-4}$ alkoxy groups, and halogen atoms. These aralkyl groups may each contain 1 to 4 substituents selected from these substituents. Specific examples of the substituents can include $C_{1-4}$ alkyl groups such as methyl, ethyl, n-propyl, isopropyl, n-butyl, isobutyl, sec-butyl and tert-butyl; hydroxyl; $C_{1-4}$ alkoxy groups such as methoxy, ethoxy, n-propoxy, isopropoxy, n-butoxy, isobutoxy, sec-butoxy and tert-butoxy; and halogen atoms such as fluorine, chlorine, bromine and iodine.

Specific examples of the substituted or unsubstituted, heterocyclic group represented by $R^1$ or $R^2$ can include 5- or 6-membered heterocyclic groups each of which contains 1 to 3 hetero atoms selected from nitrogen, oxygen and sulfur atoms, such as 2-pyridyl, 2-furyl and 2-thienyl. Illustrative of substituents on these heterocyclic groups are $C_{1-4}$ alkyl groups, hydroxyl group, $C_{1-4}$ alkoxy groups, and halogen atoms. These heterocyclic groups may each contain 1 to 4 substituents selected from these substituents. Specific examples of the substituents can include $C_{1-4}$ alkyl groups such as methyl, ethyl, n-propyl, isopropyl, n-butyl, isobutyl, sec-butyl and tert-butyl; hydroxyl; $C_{1-4}$ alkoxy groups such as methoxy, ethoxy, n-propoxy, ispropoxy, n-butoxy, isobutoxy, sec-butoxy and tert-butoxy; and halogen atoms such as fluorine, chlorine, bromine andiodine.

Specific examples of the trisubstituted silyl group represented by $R^1$ or $R^2$ can include tri($C_{1-6}$ alkyl)silyl groups such as trimethylsilyl, triethylsilyl, triisopropylsilyl, dimethylisopropylsilyl, diethylisopropylsilyl, dimethyl(2,3-dimethyl-2-butyl)silyl, tert-butyldimethylsilyl, and dimethylhexylsilyl; di($C_{1-6}$ alkyl)($C_{6-18}$ aryl)silyl groups such as dimethylcumylsilyl; di($C_{6-18}$ aryl)($C_{1-6}$ alkyl)silyl groups such as tert-butyldiphenylsilyl and diphenylmethylsilyl; tri ($C_{6-18}$ aryl)silyl groups such as triphenylsilyl; and tri($C_{7-19}$ aralkyl)silyl groups such as tribenzylsilyl and tri-p-xylylsilyl.

Specific examples of the halogen atom represented by $R^1$ or $R^2$ can include fluorine, chlorine, bromine and iodine.

Among these, preferred examples of $R^1$ and $R^2$ can include hydrogen atom; $C_{1-4}$ alkyl groups such as methyl, ethyl, propyl, isopropyl, n-butyl and tert-butyl, each of which may contain one or more substituents; alkenyl groups such as vinyl and styryl, each of which may contain one or more substituents; dialkylamino groups such as dimethylamino and diethylamino; 5- to 8-membered cyclic amino groups such as piperidino; $C_{6-10}$ aryl groups such as phenyl, 4-tolyl, 3,5-xylyl, 3,5-di(tert-butyl)-4-methoxyphenyl, naphthalen-1-yl and naphthalen-2-yl, each of which may contain one or more substituents; aralkyl groups each having 7 to 15 carbon atoms in total, such as benzyl and α-phenylethyl; heterocyclic groups such as 2-pyridyl, 2-furyl and 2-thienyl; and trialkylsilyl groups such as trimethylsilyl and tert-butyldimethylsilyl.

Particularly preferred examples of $R^1$ and $R^2$ can include hydrogen atom, methyl, ethyl, propyl, isopropyl, n-butyl, tert-butyl, trifluoromethyl, and phenyl.

Specific examples of the $C_{1-5}$ alkyl group represented by each of $R^3$ to $R^6$ can include methyl, ethyl, n-propyl, isopropyl, n-butyl, isobutyl, sec-butyl, tert-butyl, and pentyl.

Specific examples of the $C_{1-5}$ alkoxy group represented by each of $R^3$ to $R^6$ can include methoxy, ethoxy, n-propoxy, isopropoxy, n-butoxy, isobutoxy, sec-butoxy, tert-butoxy and pentoxy.

Specific examples of the di($C_{1-5}$ alkyl)amino group represented by each of $R^3$ to $R^6$ can include dimethylamino, diethylamino, di(n-propyl)amino, diisopropylamino, di(n-butyl)amino, diisobutylamino, di(sec-butyl)amino, di(tert-butyl)amino, and dipentylamino.

Specific examples of the 5- to 8-membered, cyclic amino group represented by each of $R^3$ to $R^6$ can include pyrrolidino and piperidino. Specific examples of the halogen atom represented by each of $R^3$ to $R^6$ can include fluorine, chlorine, bromine, and iodine.

Among these, preferred examples of $R^3$ to $R^6$ can include hydrogen atom; $C_{1-4}$ alkyl groups such as methyl, ethyl, propyl, isopropyl, n-butyl, and tert-butyl; alkoxy groups such as methoxy, ethoxy, n-propoxy, isopropoxy, n-butoxy, and tert-butoxy; dialkylamino groups dimethylamino and diethylamino; and 5- or 8-membered, cyclic amino groups such as pyrrolidino and piperidino.

As particularly preferred $R^3$ and $R^4$, hydrogen atoms can be mentioned.

As particularly preferred $R^5$ and $R^6$, hydrogen atoms and methoxy groups can be mentioned.

Specific examples of the $C_{1-5}$ alkyl group represented by $R^7$ can include methyl, ethyl, n-propyl, isopropyl, n-butyl, isobutyl, sec-butyl, tert-butyl, and pentyl.

Specific examples of the $C_{1-5}$ alkoxy group represented by $R^7$ can include methoxy, ethoxy, n-propoxy, isopropoxy, n-butoxy, isobutoxy, sec-butoxy, tert-butoxy and pentoxy.

Specific examples of the di($C_{1-5}$ alkyl)amino group represented by $R^7$ can include dimethylamino, diethylamino, di(n-propyl)amino, diisopropylamino, di(n-butyl)amino, diisobutylamino, di(sec-butyl)amino, di(tert-butyl)amino, and dipentylamino.

Specific examples of the 5- to 8-membered, cyclic amino group represented by $R^7$ can include pyrrolidino and piperidino.

Specific examples of the halogen atom represented by $R^7$ can include fluorine, chlorine, bromine, and iodine.

Among these, preferred examples of $R^7$ can include $C_{1-4}$ alkyl groups such as methyl, ethyl, propyl, isopropyl, n-butyl, and tert-butyl; alkoxy groups such as methoxy, ethoxy, n-propoxy, isopropoxy, n-butoxy, and tert-butoxy; dialkylamino groups dimethylamino and diethylamino; and 5- or 8-membered, cyclic amino groups such as pyrrolidino and piperidino.

As particularly preferred $R^7$, methyl and methoxy can be mentioned.

In the phosphine compound of the present invention represented by the formula (1), $R^3$ and $R^4$, $R^5$ and $R^6$, and $R^6$ and $R^7$ may each be fused together to form a fused benzene ring, a fused, substituted benzene ring, a trimethylene group, a tetramethylene group, a pentamethylene group, a methylenedioxy group, an ethylenedioxy group or a trimethylenedioxy group.

Preferred examples of such fused phosphine compounds can include those in which $R^6$ and $R^7$ are fused together to form a fused benzene ring, a fused, substituted benzene ring, a trimethylene group, a tetramethylene group, a pentamethylene roup, a methylenedioxy group, an ethylenedioxy group or a trimethylenedioxy group.

Particularly preferred examples can include fused phosphine compounds in which $R^6$ and $R^7$ are fused together to form a fused benzene ring, a fused, substituted benzene ring, a tetramethylene group, a methylenedioxy group, or an ethylenedioxy group.

As substituents on the above-described, fused, substituted benzene rings, functional groups inert to asymmetric synthetic reactions can be mentioned. The fused, substituted benzene rings may each contain 1 to 4 substituents selected from such functional groups. Specific examples of the substituents can include $C_{1-4}$ alkyl groups such as methyl, ethyl, n-propyl, isopropyl, n-butyl, isobutyl, sec-butyl and tert-butyl; hydroxyl; $C_{1-4}$ alkoxy groups such as methoxy, ethoxy, n-propoxy, isopropoxy, n-butoxy, isobutoxy, sec-butoxy and tert-butoxy; and halogen atoms such as fluorine, chlorine, bromine and iodine.

The phosphine compound (1) according to the present invention is in the form of an axially asymmetric, optically active substance (enantiomer), a racemic modification, or a mixture thereof, with a single, axially asymmetric, optically active substance (enantiomer) being particularly preferred.

Particularly preferred examples of the phosphine compound (1) according to the present invention can include phosphine compounds represented by the following formula (1'):

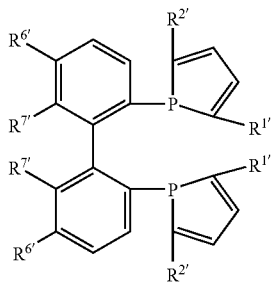

(1')

wherein $R^{1'}$ and $R^{2'}$ each independently represents a hydrogen atom, a substituted or unsubstituted $C_{1-5}$ alkyl group or a substituted or unsubstituted aryl group; $R^{6'}$ represents a hydrogen atom, a $C_{1-5}$ alkyl group, a $C_{1-5}$ alkoxy group or a halogen atom; $R^{7'}$ represents a $C_{1-5}$ alkyl group, a $C_{1-5}$ alkoxy group or a halogen atom; and $R^{6'}$ and $R^{7'}$ may be fused together to form a fused benzene ring, a fused, substituted benzene ring, a tetramethylene group, a methylenedioxy group or an ethylenedioxy group.

In the phosphine compounds of the present invention represented by the formula (1'), specific examples of the $C_{1-5}$ alkyl group represented by $R^{1'}$ or $R^{2'}$ can include methyl, ethyl, n-propyl, isopropyl, n-butyl, isobutyl, sec-butyl, tert-butyl, and pentyl. These alkyl groups may each contain 1 to 4 substituents such as halogen atoms. As specific examples of such substituted alkyl groups, trifluoromethyl and the like can be mentioned.

Specific examples of the substituted or unsubstituted aryl group reprsented by $R^{1'}$ or $R^{2'}$ can include phenyl, naphthalen-1-yl, and naphthalen-2-yl. Illustrative of substituents on the aryl group are $C_{1-4}$ alkyl groups, hydroxyl group, $C_{1-4}$ alkoxy groups, and halogen atoms. The aryl groups may each contain 1 to 5 substituents selected from these substituents. Specific examples of the substituents can include $C_{1-4}$ alkyl groups such as methyl, ethyl, n-propyl, isopropyl, n-butyl, isobutyl, sec-butyl and tert-butyl; hydroxyl; $C_{1-4}$alkoxy groups such as methoxy, ethoxy, n-propoxy, isopropoxy, n-butoxy, isobutoxy, sec-butoxy and tert-butoxy; and halogen atoms such as fluorine, chlorine, bromine and iodine.

Specific examples of the $C_{1-5}$ alkyl groups represented by $R^{6'}$ can include methyl, ethyl, n-propyl, isopropyl, n-butyl, isobutyl, sec-butyl, tert-butyl and pentyl.

Specific examples of the $C_{1-5}$ alkoxy groups represented by $R^{6'}$ can include methoxy, ethoxy, n-propoxy, isopropoxy, n-butoxy, isobutoxy, sec-butoxy, tert-butoxy and pentyloxy.

Specific examples of the halogen atom represented by $R^{6'}$ can include fluorine, chlorine, bromine and iodine.

Specific examples of the $C_{1-5}$ alkyl groups represented by $R^{7'}$ can include methyl, ethyl, n-propyl, isopropyl, n-butyl, isobutyl, sec-butyl, tert-butyl and pentyl.

Specific examples of the $C_{1-5}$ alkoxy groups represented by $R^{7'}$ can include methoxy, ethoxy, n-propoxy, isopropoxy, n-butoxy, isobutoxy, sec-butoxy, tert-butoxy and pentyloxy.

Specific examples of the halogen atom represented by $R^{7'}$ can include fluorine, chlorine, bromine and iodine.

$R^{6'}$ and $R^{7'}$ may be fused together to form a fused benzene ring, a fused, substituted benzene ring, a tetramethylene group, a methylenedioxy group or an ethylenedioxy group, with a fused benzene ring, tetramethylene group or methylenedioxy group being preferred.

The phosphine compounds (1') according to the present invention are each in the form of an axially asymmetric, optically active substance (enantiomer), a racemic modification, or a mixture thereof, with a single, axially asymmetric, optically active substance (enantiomer) being particularly preferred.

The primary phosphine compounds represented by the formula (2) are intermediates for the corresponding phosphine compounds represented by the formula (1).

As specific examples of $R^5$, $R^6$ and $R^7$ in the primary phosphine compounds represented by the formula (2), the same groups and atoms as described above can be exemplified.

The primary phosphine compounds according to the present invention are each in the form of an axially asymmetric, optcally active substance (enantiomer), a racemic modification, or a mixture thereof, with a single, axially asymmetric, optically active substance (enantiomer) being particularly preferred.

Among the phosphine compounds of the present invention, particularly preferred are primary phosphine compounds represented by the following formula (2'):

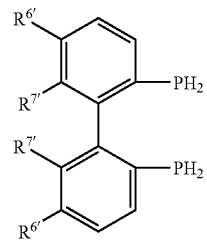

(2')

wherein $R^{5'}$, $R^{6'}$ and $R^{7'}$ have the same meanings as defined above.

The primary phosphine compounds represented by the formula (2') are intermediates for the corresponding phosphine compounds represented by the formula (1').

As specific examples of $R^{5'}$, $R^{6'}$ and $R^{7'}$ in the primary phosphine compounds represented by the formula (2'), the same groups and atoms as described above can be exemplified.

The primary phosphine compounds of the present invention represented by the formula (2') are each in the form of an axially asymmetric, optically active substance (enantiomer), a racemic modification, or a mixture thereof, with a single, axially asymmetric, optically active substance (enantiomer) being particularly preferred.

The phosphine compound (1) of the present invention can be produced, for example, in accordance with the following reaction scheme:

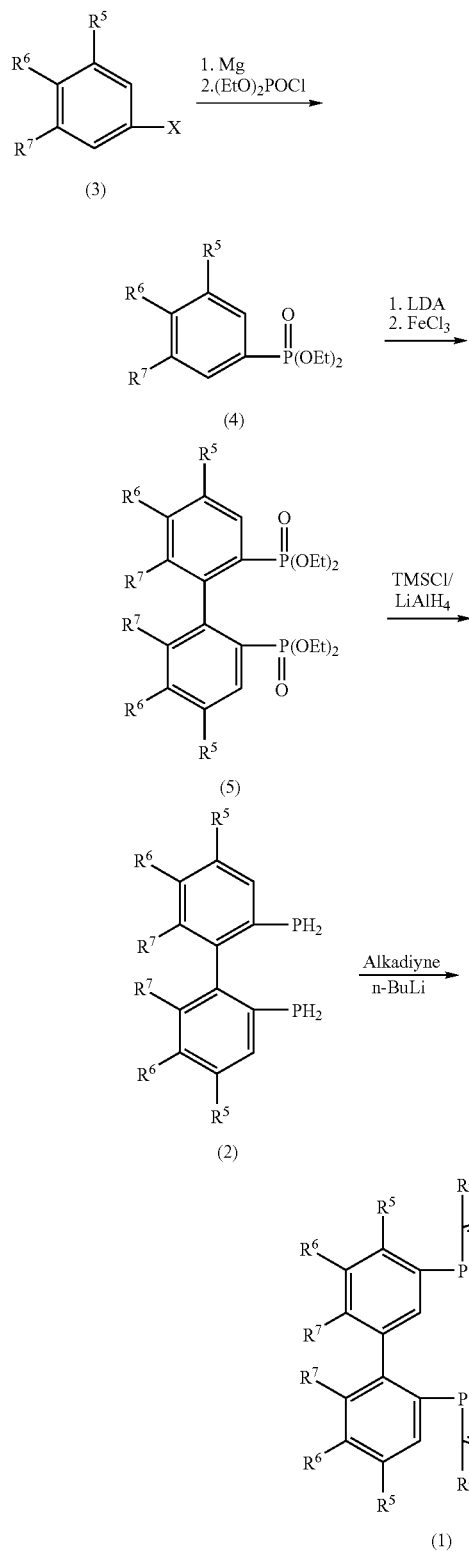

wherein X represents a halogen atom, preferably a bromine atom, and $R^1$ to $R^7$ have the same meanings as defined above.

Described specifically, excess diethyl chlorophosphate ($(EtO)_2POCl$) is reacted with a Grignard reagent, which has been obtained from a compound (3) and magnesium, in an organic solvent such as diethyl ether or tetrahydrofuran to obtain a compound (4). In the presence of lithium diisopropylamide (LDA), ferric chloride is reacted with the compound (4) to yield a compound (5). The compound (5) is then reduced with trimethylsilyl chloride (TMSCl) and lithium aluminum hydrie ($LiAlH_4$) to afford a primary phosphine represented by the formula (2). Further, an alkadiyne is reacted with the primary phosphine in the presence of an alkyllithium such as n-butyllithium or n-propyllithium to obtain the phosphine compound (1).

Taking as an example an optically active substance of a compound (7) represented by the following formula (7):

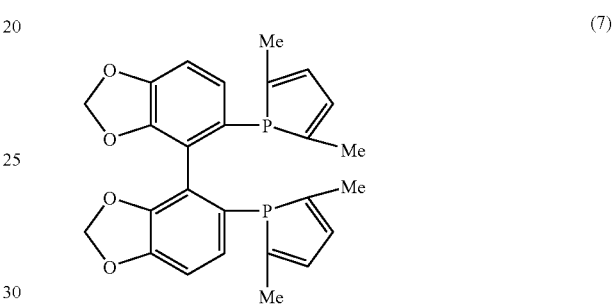

i.e., the (+)-isomer ((+)-4,4'-bi-1,3-benzodioxole)-5,5'-diylbis(2,5-dimethyl 1H-phosphole)), which may hereinafter be referred to as "(+)-MP²-SEGPHOS", to avoid complexity, a production process of the compound according to the present invention will be described specifically. It should however be borne in mind that the present invention is not limited to this example.

(+)-MP²-SEGPHOS can be produced by the process shown in the following reaction scheme.

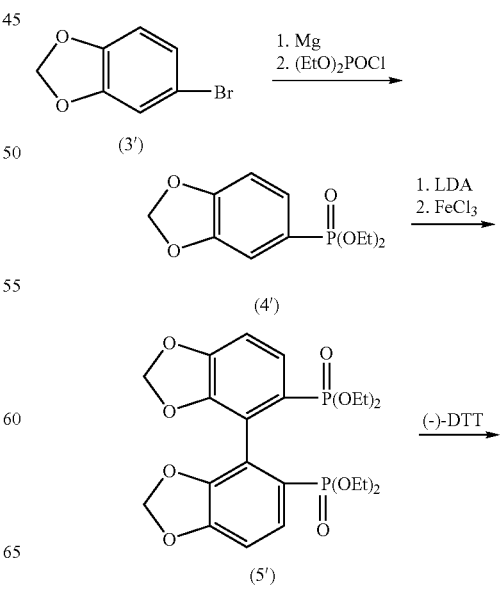

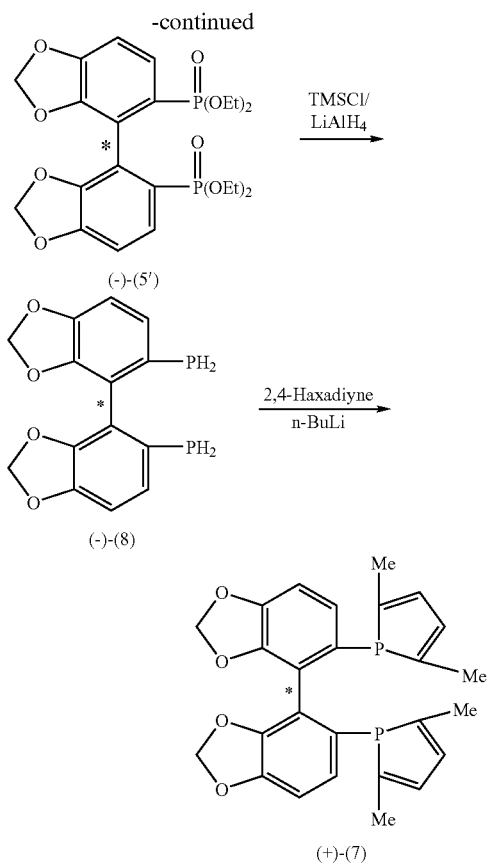

Wherein * indicates axially asymmetric optical activity.

A Grignard reagent, which has been prepared from 3,4-methylenedioxyphenyl bromide (3'), and diethyl chlorophosphate are reacted to synthesize a phosphonate (4'). Ferric chloride ($FeCl_3$) is then added to the phosphonate (4') in the presence of lithium diisopropylamide to yield a diphosphate (5') as a racemic compound (see, JP 2000-16998 A, Example 4). After the racemic modification of the diphosphate (5') obtained as described above, is optically resolved using (−)-toluoyltartaric acid ((−)-DTT), reduction is conducted with trimethylsilyl chloride (TMSCl)/lithium aluminum hydride ($LiAlH_4$) to afford ((−)-4,4'-bi-1,3-benzodioxole)-5,5'-diylbisphosphine (8)) which may hereinafter be referred to as "(−)-$H^2$-SEGPHOS". Finally, the compound (8) is reacted with 2,4-hexadiyne in the presence of n-butyllithium to yield the target compound, (+)-$MP^2$-SEGPHOS ((+)-(7)).

Further, (+)-$H^2$-SEGPHOS is obtained by conducting optical resolution with (+)-toluoyltartaric acid, while (−)-$MP^2$-SEGPHOS is obtained with (+)-$H^2$-SEGPHOS.

The optical active compound (7) can be obtained from recemic compound (7) using optically active column or the like. The optical active compound (2), on the other hand, can also be obtained from recemic compound (2) using optically active column or the like.

Concerning the compounds in which $R^1$ and $R^2$ are other than methyl groups, the target compounds can be obtained using the corresponding alkadiynes in place of 2,4-hexadiyne. Illustrative of the corresponding alkadiynes are 3,5-octadiyne, 4,6-decadiyne, 2,7-dimethyl-3,5-octadiyne, 5,7-dodecadiyne, 3,8-dimethyl-4,6-decadiyne, 2,9-dimethyl-4,6-decadiyne, 2,2,7,7-tetramethyl-3,5-octadiyne, 6,8-tetradecadiyne, 4,9-diemthyl-5,7-dodecadiyne, 2,11-dimethyl-5,7-dodecadiyne, 1,1,1,6,6,6-hexafluoro-2,4-hexadiyne, 1,3-diphenylbutadiyne, 1,3-bis(4-tolyl)-butadiyne, 1,3-bis(3,5-xylyl)-butadiyne, 1,3-bis(naphthalen-1-yl)-butadiyne, 1,3-bis(naphthalen-2-yl)-butadiyne, and 1,3-bis(3,5-di(tert-butyl)-4-methoxyphenyl)-butadiyne.

The phosphine compounds (1) of the present invention and the primary phosphine compounds of the present invention represented by the formula (2), which are other than those containing a hydrogen atom as $R^5$ and a methylenedioxy group as a fused group formed by $R^6$ and $R^7$, can be produced by using, instead of 3,4-methylenedioxyphenyl bromide, other aryl halogenides. Specific examples can include 3-methoxyphenyl bromide, 3-ethoxyphenyl bromide, 3-methylphenyl bromide, 3-ethylphenyl bromide, 3,4-ethylenedioxyphenyl bromide, 3,4-trimethylenedioxyphenyl bromide, and 2-naphthyl bromide.

The above-described process can be similarly used to obtain the phosphine compounds (1) and primary phosphine compounds represented by the formula (2) other than those containing methyl groups as $R^1$ and $R^2$, hydrogen atoms as $R^3$, $R^4$ and $R^5$ and a methylenedioxy group as a fused group formed by $R^6$ and $R^7$.

The phosphine compounds (1) of this invention obtained as described above, as ligands, form transition metal phosphine complexes. Examples of transition metals useful in forming these complexes can include iridium, rhodium, ruthenium, palladium, nickel, copper and platinum. Preferred examples of complexes so formed can include transition metaphosphine complexes represented by the following formula (9):

wherein M is a transition metal selected from the group consisting of iridium, rhodium, ruthenium, palladium, nickel, copper and platinum; L is a phosphine compound represented by the formula (1); W, U, m, n, p, q, r and s are (a) when M is iridium or rhodium, (i) W is chlorine, bromine or iodine, m=n=p=1, r=2, and q=s=0, (ii) W is 1,5-cyclooctadiene or norbonadiene, Z is $BF_4$, $ClO_4$, OTf (Tf: triflate group ($SO_3CF_3$)), $PF_3$, $SbF_6$ or $BPh_4$ (Ph: phenyl group), m=n=p=r=s=1, and q=0, (iii) Z is $BF_4$, $ClO_4$, OTf, $PF_3$, $SbF_6$ or $BPh_4$, m=r=s=1, n=2, and q=0, (b) when M is ruthenium, (i) W is chlorine, bromine or iodine, Z is a trialkylamine, m=p=s=1, n=r=2, and q=0, (ii) W is chlorine, bromine or iodine, Z is a pyridyl group or ring-substituted pyridyl group, m=n=r=1, p=2, and q=0, (iii) W is a carboxylate group, m=n=r=1, p=2, and q=s=0, (iv) W is chlorine, bromine or iodine, Z is dimethyl formamide or dimethylacetamide, m=n=r=1, p=2, q=0, and s stands for an integer of from 0 to 4, (v) W is chlorine, bromine or iodine, U is chlorine, bromine or iodine, Z is a dialkylammonium ion, m=n=p=2, q=3, and r=s=1, (vi) W is chlorine, bromine or iodine, U is an aromatic compound or olefin as a neutral ligand, Z is chlorine, bromine, iodine or $I_1$, and m=n=p=q=r=s=1, (vii) Z is $BF_4$, $ClO_4$, OTf, $PF_6$, $SbF_6$ or $BPh_4$, m=n=r=1, p=q=0, and s=2, (viii) W and U may be the same or different and are each a hydrogen atom, chlorine, bromine, carboxyl group or a still further anion group, Z is a diamine compound, and m=n=p=q=r=s=1, (c) when M is palladium, (i) W is chlorine, bromine or iodine, m=n=r=1, p=2, and q=s=0, (ii) W is an allyl group, m=n=p=r=1, q=s=0, (iii) Z is $BF_4$, $ClO_4$, OTf, $PF_6$, $SbF_6$ or $BPh_4$, m=n=r=1, p=q=0, and s=2, (iv) W is a $C_{1-5}$ alkylnitrile, benzonitrile, phthalonitrile, pyridine, dimethylsulfoxide, dimethylformamide, dimethylacetamide or acetone, Z is $BF_4$, $ClO_4$, OTf, $PF_6$, $SbF_6$ or $BPh_4$, m=n=r=1, p=s=2, and q=0, (d) when M is a nickel, (i) W is chlorine, bromine or iodine, m=n=r=1, p=2, and q=s=0, (ii) Z is $BF_4$, $ClO_4$, OTf, $PF_6$, $SbF_6$ or $BPh_4$, m=n=r=1, p=q=0, and s=2, (e) when M is copper, W is hydrogen atom, fluorine, chlorine, bromine or iodine, m=p=4, n=2, r=1, q=s=0, (f) when M is platinum, (i) W is a $C_{1-5}$ alkylnitrile, benzonitrile, phthalonitrile, pyridine, dimethylsulfoxide, dimethylformamide, dimethylacetamide or acetone, Z is $BF_4$, $ClO_4$, OTf, $PF_6$, $SbF_6$ or $BPh_4$, m=n=r=1, p=s=2, and q=0, (ii) W is chlorine, bromine or iodine, m=n=r=1, p=2, and q=s=0, (iii) W is chlorine, bromine or iodine, U is $SnCl_2$, m=n=q=r=1, p=2, and s=0, and (iv) W is chlorine, bromine or iodine, U is $SnCl_3$, m=n=p=q=r=1, and s=0.

No particular limitation is imposed on the production process of the transition metal phosphine complexes (9). For example, however, they can be produced by a process to be described next or by its equivalent process. In the formulas of transition metal phosphine complexes to be described below, the following abbreviations will be employed: cod: 1,5-cyclooctadine, nbd: norbornadiene, Ac: acetyl group, acac: acetyl acetonate, dmf: dimethylformamide, en: ethylenediamine, DPEN: diphenylethylenediamine, and Tf: trifluoromethanesulfonyl group.

Rhodium complexes: As a specific example of production of a rhodium complex, it can be synthesized, for example, by reacting bis(1,5-cyclooctadiene)rhodium(I) tetrafluoroborate ([Rh(cod)$_2$]BF$_4$) and a phosphine compound (1) of the present invention in accordance with the procedure described in "Jikken Kagaku Koza (Experimental Chemistry Series), 4$^{th}$ edition" compiled by The Chemical Society of Japan, 18 (Organometallic Complexes), 339–344, 1991 (Maruzen).

Specific examples of rhodium complexes can include [Rh(L)Cl]$_2$, [Rh(L)Br]$_2$, [Rh(L)I]$_2$, [Rh(cod)(L)]OTf, [Rh(cod)(L)]BF$_4$, [Rh(cod)(L)]ClO$_4$, [Rh(cod)(L)]SbF$_6$, [Rh(cod)(L)]PF$_6$, [Rh(cod)(L)]BPh$_4$, [Rh(nbd)(L)]OTf, [Rh(nbd)(L)]BF$_4$, [Rh(nbd)(L)]ClO$_4$, [Rh(nbd)(L)]SbF$_6$, [Rh(nbd)(L)]PF$_6$, [Rh(nbd)(L)]BPh$_4$, [Rh (L)$_2$]OTf, [Rh(L)$_2$]BF$_4$, [Rh(L)$_2$]ClO$_4$, [Rh(L)$_2$]SbF$_6$, [Rh(L)$_2$]PF$_6$, and [Rh(L)$_2$]BPh$_4$.

Ruthenium complexes: As a process for producing a ruthenium complex, it can be prepared, for example, by heating (1,5-cyclooctadiene) dichlororuthenium ([Ru(cod) Cl$_2$]$_n$) and a phosphine compound (1) of the present invention under reflux in the presence of a trialkylamine in an organic solvent in accordance with the procedure described in a journal (J. Chem. Soc., Chem. Commun., 922, 1985). It can also be produced, for example, by heating bis[dichloro(benzene)ruthenium] ([Ru (benzene) Cl$_2$]$_2$) and a phosphine compound (1) of the present invention in the presence of a dialkylamine under reflux in an organic solvent in accordance with the procedure described in JP 11-269185 A. It can also be produced, for example, by heating bis[diiodo(para-cymene)ruthenium] ([Ru (p-cymene)I$_2$]$_2$) and a phosphine compound (1) of the present invention under stirring in an organic solvent in accordance with the procedure disclosed in a journal (J. Chem. Soc., Chem. Commun., 1208, 1989). Further, it can also be synthesized, for example, by reacting Ru$_2$Cl$_4$(L)$_2$NEt$_3$, which has been obtained following the procedure of a journal (J. Chem. Soc., Chem. Commun., 992, 1985), and a diamine compound in an organic solvent in accordance with the procedure disclosed in JP 11-189600 A.

Specific examples of ruthenium complexes can include Ru(OAc)$_2$(L), Ru(OCOCF$_3$)$_2$(L), Ru$_2$Cl$_4$(L)$_2$NEt$_3$, [[RuCl(L)]$_2$ (μ-Cl)$_3$][Me$_2$NH$_2$], [[RuBr(L)]$_2$ (μ-Br)$_3$][Me$_2$NH$_2$], [[RuI(L)]$_2$(μ-I)$_3$][Me$_2$NH$_2$], [[RuCl(L)]$_2$(μ-Cl)$_3$][Et$_2$NH$_2$], [[RuBr (L)]$_2$(μ-Br)$_3$][Et$_2$NH$_2$], [[RuI(L)]$_2$(μ-I)$_3$][Et$_2$NH$_2$], RuCl$_2$(L), RuBr$_2$(L), RuI$_2$(L), [RuCl$_2$(L)](dmf)$_n$, RuCl$_2$(L) (pyridine)$_2$, RuBr$_2$(L)(pyridine)$_2$, RuI$_2$(L)(pyridine)$_2$, RuCl$_2$(L)(2,2'-dipyridine), RuBr$_2$(L)(2,2'-dipyridine), RuI$_2$(L)(2,2'-dipyridine), [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [RuI(p-cymene)(L)]I$_3$, [Ru(L)](OTf)$_2$, [Ru(L)](BF$_4$)$_2$, [Ru(L)](ClO$_4$)$_2$, [Ru(L)](SbF$_6$)$_2$, [Ru(L)](PF$_6$)$_2$, [Ru(L)](BPh$_4$)$_2$, [RuCl$_2$(L)](en), [RuBr$_2$ (L)](en), [RuI$_2$(L)](en) [RuH$_2$(L)](en), [RuCl$_2$ (L)](DPEN), RuBr$_2$(L)](DPEN), [RuI$_2$(L)](DPEN), and [RuH$_2$(L)](DPEN).

Iridium complexes: As a process for producing an iridium complex, it can be prepared, for example, by reacting a phosphine compound (1) of the present invention and [(1,5-cyclooctadiene)(acetonitrile)iridium] tetrahydroborate ([Ir(cod)(CH$_3$CN)$_2$]B$_4$) under stirring in an organic solvent in accordance with the procedure described in a journal (J. Organomet. Chem., 428, 213, 1992).

Specific examples of iridium complexes can include [Ir(L)Cl]$_2$, [Ir(L)Br]$_2$, [Ir(L)I]$_2$, [Ir(cod)(L)]OTf, Ir(cod)(L)]BF$_4$, [Ir(cod)(L)]ClO$_4$, [Ir(cod)(L)]SbF$_6$, [Ir(cod)(L)]PF$_6$, [Ir(cod)(L)]BPh$_4$, [Ir(nbd)(L)]OTf, [Ir(nbd)(L)]BF$_4$, [Ir(nbd)(L)]ClO$_4$, [Ir(nbd)(L)]SbF$_6$, [Ir(nbd)(L)]PF$_6$, [Ir(nbd)(L)]BPh$_4$, [Ir(L)$_2$]OTf, [Ir(L)$_2$]BF$_4$, [Ir(L)$_2$]ClO$_4$, [Ir(L)$_2$]SbF$_6$, [Ir(L)$_2$]PF$_6$, [Ir(L)$_2$]BPh$_4$, IrCl(cod)(CO)(L), IrBr(cod)(CO)(L), and IrI(cod)(CO)(L).

Palladium complexes: As a process for producing a palladium complex, it can be prepared, for example, by reacting a phosphine compound (1) of the present invention and π-allylpalladium chloride ([(π-allyl]PdCl)$_2$) in accordance with the procedure described in journals (J. Am. Chem. Soc., 113, 9887, 1991; J. Chem. Soc., Dalton, Trans., 2246–2249, 1980; Tetrahedron Letters, 37, 6351–6354, 1996).

Specific examples of palladium complexes can include PdCl$_2$(L), PdBr$_2$(L), PdI$_2$(L), Pd(OAc)$_2$(L), Pd(OCOCF$_3$)$_2$(L), [(π-allyl)Pd(L)]Cl, [(π-allyl)Pd(L)]Br, [(π-allyl)Pd(L)]I, [(π-allyl)Pd(L)]OTf, [(π-allyl)Pd(L)]BF$_4$, [(π-allyl)Pd(L)]ClO$_4$, [(π-allyl)Pd(L)]SbF$_6$, [(π-allyl)Pd(L)]PF$_6$, [(π-allyl)Pd(L)]BPh$_4$, [(Pd(L))](OTf)$_2$, [(Pd(L))](BF$_4$)$_2$, [(Pd(L))](ClO$_4$)$_2$, [[(Pd (L))](SbF$_6$)$_2$, [(Pd(L))](PF$_6$)$_2$, [(Pd(L))](BPh$_4$)$_2$, PhCH$_2$Pd(L)Cl, PhCH$_2$Pd(L)Br, PhCH$_2$Pd(L)I, PhPdCl(L), PhPdBr(L), PhPdI(L), Pd(L), and [Pd(L)(PhCN)$_2$](BF$_4$)$_2$.

Nickel complexes: As a process for producing a nickel complex, it can be prepared, for example, by dissolving a phosphine compound (1) of the present invention and nickel chloride (NiCl$_2$) in an organic solvent and heating the resultant mixture under stirring in accordance with the procedure described in "Jikken Kagaku Koza (Experimental Chemistry Series), 4$^{th}$ edition" compiled by The Chemical Society of Japan, 18 (Organometallic Complexes), 376, 1991 (Maruzen) or the procedure described in a journal (J. Am. Chem. Soc., 113, 9887, 1991).

Specific examples of nickel complexes can include NiCl$_2$(L), NiBr$_2$ (L), and NiI$_2$ (L).

Copper complexes: As a process for producing a copper complex, it can be prepared, for example, by dissolving a phosphine compound (1) of the present invention and copper (I) chloride (CuCl$_2$) in an organic solvent and heating the resultant mixture under stirring in accordance with the procedure described in "Jikken Kagaku Koza (Experimental Chemistry Series), 4$^{th}$ edition" compiled by The Chemical Society of Japan, 18 (Organometallic Complexes), 444–445, 1991 (Maruzen).

Specific examples of copper complexes can include $Cu_4F_4(L)_2$, $Cu_4Cl_4(L)_2$, $Cu_4Br_4(L)_2$, $Cu_4I_4(L)_2$, and $Cu_4H_4(L)_2$.

Platinum complexes: As a process for producing a platinum complex, it can be prepared, for example, by dissolving a phosphine compound (1) of the present invention and dibenzonitrile dichloroplatinum ($PtCl_2(PhCN)_2$) in an organic solvent and heating the resultant mixture under stirring in accordance with the procedure described in a journal (Organometallics, 10, 2046, 1991). A Lewis acid ($SnCl_2$ or the like) may be added as needed.

Specific examples of platinum complexes can include $PtCl_2(L)$, $PtBr_2(L)$, $PtI_2(L)$, $PtCl_2(L)$, ($SnCl_2$) and $PtCl(L)(SnCl_3)$.

The transition metal phosphine complexes, which contain as ligands the optically active compounds (especially, enantiomers) of the phosphine compounds (1) of the present invention, are useful as transition metal complex catalysts for asymmetric synthesis reactions, especially as transition metal complex catalysts for asymmetric hydrogenation reactions, transition metal complex catalysts for asymmetric isomerization reactions, transition metal complex catalysts for asymmetric hydroformylation reactions, and the like. In the phosphine compounds (1) of the present invention, their racemic modifications are also useful as production intermediates for their corresponding, optically active compounds.

When these transition metal phosphine complexes are used as catalysts, the complexes may be used without purification although they may be used after heightening them in purity.

These transition metal phosphine complexes, especially transition metal phosphine complexes—each of which contains ruthenium and (4,4'-bi-1,3-benzodioxole)-5,5'-diylbis(2,5-dimethylphosp hole)(MP$^2$-SEGPHOS), an optically active compound, as a ligand—can provide higher enantioselectively than complexes—each of which contains BINAP or SEGPHOS, an optically active compound having a similar biaryl moiety, as a ligand—in asymmetric hydrogenation of N-acetamidocinnamic acid.

When conducting asymmetric hydrogenation reactions by using transition metal phosphine complexes of the present invention, substrates to be subjected to asymmetric hydrogenation can be carbonyl compounds, imines, and olefins. Specific examples can include α-ketoesters, β-ketoesters, γ-ketoesters, α-hydroxyketones, β-hydroxyketones, allylketones, α,β-unsaturated ketones, enamides, enolesters, allyl alcohols and α,β-unsaturated carboxylic acids, with α,β-unsaturated carboxylic acids being preferred.

Upon conducting an asymmetric hydrogenation reaction with a transition metal phosphine complex of the present invention, reaction conditions cannot be specified in a wholesale manner because they can vary depending on the substrate to be used, the complex and the like. In general, however, the reaction may be conducted at a reaction temperature of from 0 to 100° C. under a hydrogen pressure of from 1.0 to 10.0 MPa for 2 to 30 hours. The transition metal phosphine complex of the present invention can be used at a molar ratio of from 1/500 to 1/10,0000 or so relative to the substrate. Any reaction solvent can be used insofar as it is stable and gives no adverse effect to the substrate or the reaction product. Specific examples of the reaction solvent can include lower alcohols such as methanol, ethanol and isopropanol, ethers such as tetrahydrofuran, and halogenated hydrocarbons such as methylene chloride and chlorobenzene. The amount of the reaction solvent to be used cannot be specified in a wholesale manner because it can vary depending on the solubility of the substrate and other parameters. In general, however, the reaction solvent can be used in a volume (mL/g) approximately 0.1 to 100 times as much as the weight part of the substrate.

EXAMPLES

Based on Examples, the present invention will hereinafter be described in detail. It should, however, be borne in mind that the present invention is by no means limited by the Examples. The following instruments were used in the measurement of physical properties in each Example.

$^1$HNMR: NMR spectrometer "DRX500 (500 MHz)" (trade name) manufactured by Bruker BioSpin Corporation.

$^1$PNMR: NMR spectrometer "DRX500 (202 MHz)" (trade name) manufactured by Bruker BioSpin Corporation.

Melting point: Micro melting point meter "MP-500D" (trade name) manufactured by Yanaco Analytical Instruments Corp.

Rotation: Optical rotation meter "DIP-4" (trade name) manufactured by JASCO.

Gas chromatography: Gas chromatograph "5890-II" (trade name) manufactured by Hewlett-Packard Company.

High-performance liquid chromatography: HPLC "HP1100" (trade name) manufactured by Hewlett-Packard Company.

Mass spectrometry: Mass spectrometer "M-80B" (trade name) manufactured by Hitachi, Ltd.

Example 1

Synthesis of (+)-(4',4'-bi-1,3-benzodixol)-5,5'-diyl-bis(2,5-dime thylphosphole)((+)-MP$^2$-SEGPHOS)

(a) Synthesis of (−)-(4',4'-bi-1,3-benzodixol)-5,5'-diylbis(diethylpho sphonate)((−)-5')

To a mixture of a diphosphate (6) (204.5 g, 478 mmol) which had been obtained by the procedure disclosed in Example 4 of JP 2000-16998 A, and (−)-ditoluoyltartaric acid (153.6 g, 478 mmol), butyl acetate (510 mL) was added, followed by heating to 105° C. The reaction mixture was allowed to cool down to room temperature. After stirred overnight, the resulting solid was collected by filtration. Dichloromethane (1,000 mL) and a 1 mol/L aqueous solution of sodium hydroxide (1,000 mL) were added. The resulting mixture was stirred for 0.5 hour, and was then allowed to separate into layers. The organic layer was washed successively with water and a saturated aqueous solution of sodium chloride, and was then dried over anhydrous sodium sulfate. The solvent was distilled off to afford the title compound (55.0 g) of 98.2% ee optical purity.

To the whole title compound (55.0 g, 106 mmol) so obtained, (−)-ditoluoyltartaric acid (41.3 g, 106 mmol) and butyl acetate (137 mL) were added, and the resulting mixture was heated under reflux. After the reaction mixture was allowed to cool down in the air, the resulting solid was collected by filtration, followed by the addition of dichloromethane (500 mL) and a 1 mol/L aqueous solution of sodium hydroxide (500 mL). Subsequent to mixing for 0.5 hour, the organic layer was washed successively with a 1 mol/L aqueous solution of sodium hydroxide, water and brine, and was then dried over anhydrous sodium sulfate. The solvent was distilled off under reduced pressure to afford the title compound (43.7 g) of >99.9% ee optical purity (yield: 21%). The optical purity was measured by HPLC.

[α]D24: −50.5 (c 1.0, CHCl$_3$).

(b) Synthesis of (−)-(4',4'-bi-1,3-benzodixol)-5,5'-diylbisphosphine (−)-H$^2$-SEGPHOS: (−)-8)

A solution of lithium aluminum hydride (19.3 g, 50.9 mmol) in tetrahydrofuran was cooled to −30° C., into which chlorotrimethylsilane (64.7 mL, 50.9 mmol) was added dropwise while maintaining the resulting mixture below −20° C. After the mixture was stirred at −30° C. for 30 minutes, a solution of the (−)-diphosphate ((−)-6) (43.7 g, 8.49 mmol) in tetrahydrofuran (150 mL) was added. Subsequent to stirring at room temperature for 1 hour, a mixed solution composed of methanol (20 mL) and tetrahydrofuran (60 mL) was added dropwise with care. Methanol (20 mL), water (40 mL) and a 1 mol/L aqueous solution of sodium hydroxide were then added successively, and the mixture so prepared was stirred. The solid was filtered off through celite, and the solvent was distilled off under reduced pressure to afford the title compound (22.7 g, yield: 87%, 99.8% ee). Incidentally, the optical purity was measured using HPLC (Chiralcel OD) equipped with an optically active column.

EI-MS: m/z 307 (M+1)+

$^1$H NMR (CDCl$_3$) δ: 3.59(4H, d, J=203.5 Hz), 5.90(4H, s), 6.75(2H, d, J=7.6 Hz), 7.13(2H, m).

$^{31}$P NMR(CDCl$_3$) δ: 130.3(t, J=202.4 Hz).

[α]D24: −58.0 (c 1.0, CHCl$_3$).

(c) Synthesis of (+)-[(4',4'-bi-1,3-benzodixol)-5,5'-diyl]bis(2,5-dime thylphosphole)((+)-MP$^2$-SEGPHOS)

(−)-H$^2$-SEGPHOS (3.4 g, 11.1 mmol) and 2,4-hexadiyne (4.5 g, 2 eq.) were dissolved with toluene (50 mL) and tetrahydrofuran (10 mL), followed by heating to 40° C. Into the mixture, a 1.6 mol/L solution of n-butyllithium in hexane (3.5 mL, 0.5 eq.) was added dropwise. Subsequent to stirring at 40° C. for 2 hours, methanol was charged, and then, the solvent was distilled off. The residue was purified by silica gel chromatography to afford the title compound (604 mg, yield: 13%, optical purity: 99.6% ee). Incidentally, the optical purity was measured using HPLC (Chiralcel OD) equipped with an optically active column.

Mp: 228 to 230° C.

EI-MS: m/z 462 ([M]+)

$^1$HNMR (CDCl$_3$) δ: 2.00(6H, s), 2.03(6H, s), 5.94(2H, d, J=1.1 Hz), 6.03(2H, d, J=1.1 Hz), 6.30–6.53(6H, m), 6.77 (2H, d, J=8.2 Hz).

$^{31}$P NMR(CDCl$_3$) δ: 3.2(s).

[α]D24: +134.70 (c 1.0, CHCl$_3$).

Example 2

Synthesis of (+)-[(4',4'-bi-1,3-benzodixol)-5,5'-diyl]bis(2,5-di methylphosphole)((+)-P$^3$-SEGPHOS)

(−)-H$^2$-SEGPHOS (3.0 g, 9.8 mmol) and 2,4-diphenylbutadiyne (3.96 g, 19.6 mmol) were dissolved with toluene (90 mL) and tetrahydrofuran (3 mL), followed by cooling to 0° C. Into the mixture, a 1.6 mol/L solution of n-butyllithium in hexane (2.45 mL, 3.92 mmol) was added dropwise. Subsequent to stirring the reaction mixture at 0° C. for 2 hours, the reaction mixture was heated to room temperature and then stirred further for 2 hours. Methanol was charged, and then, the solvent was distilled off. The residue was purified by silica gel chromatography to afford the title compound (3.29 g, yield: 47%, optical purity: 99.7% ee). Incidentally, the optical purity was measured using HPLC (Chiralcel OD) equipped with an optically active column.

EI-MS: m/z 711 (M+1)+

$^1$H NMR (CDCl$_3$) δ: 5.23(2H, d, J=1.6 Hz), 5.57(2H, d, J=1.6 Hz), 6.62(2H, d, J=8.2 Hz), 6.69(2H, td, J=2.2, 8.2 Hz), 6.74–8.10(24H, m).

$^{31}$P NMR(CDCl$_3$) δ: −1.8(s).

[α]D24: +164.3 (c 1.0, CHCl$_3$).

Example 3

Synthesis of [Rh(cod)((+)-MP$^2$-SEGPHOS)]OTf (+)-MP$^2$-SEGPHOS (50 mg, 0.108 mmol) was dissolved in dichloromethane (3 mL), and the resulting solution was added dropwise into a mixture of [Rh(cod)$_2$]OTf (50.6 mg, 0.108 mmol) and dichloromethane (3 mL). Subsequent to stirring at room temperature for 4 hours, the solvent was distilled off under reduced pressure. The solid was washed three times with 5 ml of hexane, and then dried under reduced pressure to afford the title compound (90 mg).

$^{31}$P NMR(CD$_2$Cl$_2$) δ: 39.6(d, J=130.5 Hz).

Example 4

Synthesis of [RuCl(p-cymene)((+)-MP$^2$-SEGPHOS)]Cl (+)-MP$^2$-SEGPHOS (50.0 mg, 0.108 mmol) and [RuCl$_2$(p-cymene)]$_2$ (33.1 mg, 0.054 mmol) were dissolved in a mixture of dichloromethane (2.5 mL) and ethanol (2.5 mL), and the resulting mixture was stirred at 50° C. for 4 hours. The solvent was then distilled off under reduced pressure to afford the title compound (76 mg, yield: 92%).

$^{31}$P NMR(CD$_2$Cl$_2$) δ: 41.4(d, J=58.0 Hz), 45.6(d, J=58.0 Hz).

Example 5

Synthesis of Ru(OAc)$_2$((+)-MP$^2$-SEGPHOS)

(+)-MP$^2$-SEGPHOS (100.0 mg, 0.216 mmol) and [RuCl$_2$(p-cymene)]$_2$ (66.1 mg, 0.108 mmol) were dissolved in a mixture of dichloromethane (2.5 mL) and ethanol (2.5 mL), and the resulting mixture was stirred at 50° C. for 4 hours. The solvent was then distilled off under reduced pressure. Sodium acetate (53.2 mg, 0.648 mmol) and 1,4-dioxane (5 mL) were then added, followed by overnight stirring at 100° C. After the reaction mixture was filtered, the solvent was distilled off under reduced pressure from the filtrate to afford the title compound (154 mg, yield: 92%).

$^{31}$P NMR(CD$_2$Cl$_2$) δ: 83.4(s).

Example 6

Synthesis of [Rh(cod)((+)-P$^3$-SEGPHOS)]OTf (+)-P$^3$-SEGPHOS (50.0 mg, 0.070 mmol) was dissolved in dichloromethane (3 mL), and the resulting solution was added dropwise into a mixture of [Rh(cod)$_2$]OTf (32.9 mg, 0.070 mmol) and dichloromethane (3 mL). Subsequent to stirring at room temperature for 4 hours, the solvent was distilled off under reduced pressure. The solid was washed three times with 5 ml of hexane, and then dried under reduced pressure to afford the title compound (79 mg).

$^{31}$P NMR(CD$_2$Cl$_2$) δ: 24.7(d, J=136.1 Hz).

Example 7

Asymmetric hydrogenation reaction of N-acetamidocinnamic acid

Under a nitrogen atmosphere, [RuCl(p-cymene)(L)]Cl (0.0024 mmol), N-acetamidocinnamic acid (100 mg, 0.487 mmol), sodium methoxide (29.1 mg, >95%, 0.511 mmol) and methanol (1 mL) were charged in a stainless steel autoclave, and under conditions of 60° C. and 3.0 MPa hydrogen pressure, the contents were stirred for 15 hours. The conversion and optical purity of the reaction product were determined by $^1$H NMR (CD$_3$OD) and HPLC, respectively. As a comparative example, a similar reaction was conducted using a similar ruthenium complex catalyst as that employed in the above asymmetric hydrogenation except for the replacement of L by (S)-SEGPHOS.

The results are presented in Table 1.

TABLE 1

| | L | Conversion (%) | Optical purity (% ee) |
|---|---|---|---|
| Example 7 | (+)-MP$^2$-SEGPHOS | 83 | 60 |
| Comp. Ex. | (S)-SEGPHOS | >99 | 28 |

In Example 7 in which hydrogenation was conducted using the transition metal complex catalyst with MP$^2$-SEGPHOS of the present invention contained as a ligand therein, the optical purity was 60% ee, that is, was excellent. Moreover, the conversion was 83%, which can be considered to be a sufficiently high value. This conversion is in such a range that use of a little longer reaction time can bring it to an industrially acceptable level. In the comparative example in which hydrogenation was conducted by using SEGPHOS having a similar biaryl skeleton, the optical purity was 28% ee, that is, extremely low although the conversion was higher than 99%, that is, superb. From the above-described results, it is understood that MP$^2$-SEGPHOS according to the present invention is an extremely useful ligand in conducting asymmetric hydrogenation.

The invention claimed is:

1. A primary phosphine compound represented by the following formula (2):

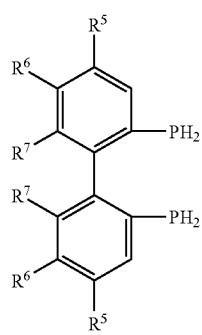

(2)

wherein R$^5$ and R$^6$ each independently represents a hydrogen atom, a C$_{1-5}$ alkyl group, a C$_{1-5}$ alkoxy group, a di(C$_{1-5}$ alkyl)amino group, a 5- to 8-membered cyclic amino group or a halogen atom; R$^7$ represents a C$_{1-5}$ alkyl group, a C$_{1-5}$ alkoxy group, a di(C$_{1-5}$ alkyl)amino group, a 5- to 8-membered cyclic amino group or a halogen atom; and at least one R$^5$ and R$^6$, and R$^6$ and R$^7$ pair is fused together to form at least one of a trimethylene group, a tetramethylene group, a pentamethylene group, a methylenedioxy group, an ethylenedioxy group and a trimethylenedioxy group.

2. A primary phosphine compound according to claim 1, which is an axially asymmetric, optically active substance.

3. A transition metal phosphine complex, comprising:
the phosphine compound according to claim 1, contained as a ligand therein, and a transition metal.

4. A transition metal phosphine complex, obtained by causing a transition metal compound to act on a phosphine compound according to claim 1.

5. The transition metal phosphine complex according to claim 3, wherein said transition metal is at least one transition metal selected from the group consisting of iridium, rhodium, ruthenium, palladium, nickel, copper and platinum.

6. The transition metal phosphine complex according to claim 4, wherein said transition metal is at least one transition metal selected from the group consisting of iridium, rhodium, ruthenium, palladium, nickel, copper and platinum.

7. The primary phosphine compound according to claim 1, wherein at least one pair of each of R$^5$ and R$^6$, and R$^6$ and R$^7$ are fused together to form at least one of a trimethylene group, a tetramethylene group, a pentamethylene group, a methylenedioxy group, an ethylenedioxy group, and a trimethylenedioxy group.

8. The primary phosphine compound according to claim 1, wherein at least one R$^5$ and R$^6$ group is fused together to form a trimethylene group, a tetramethylene group, a pentamethylene group, a methylenedioxy group, an ethylenedioxy group, or a trimethylenedioxy group.

9. The primary phosphine compound according to claim 1, wherein at least one R$^6$ and R$^7$ group is fused together to form at least one of a trimethylene group, a tetramethylene group, a pentamethylene group, a methylenedioxy group, an ethylenedioxy group, and a trimethylenedioxy group.

10. The primary phosphine compound according to claim 1, wherein both R$^5$ and R$^6$ pairs are each fused together to independently form a trimethylene group, a tetramethylene group, a pentamethylene group, a methylenedioxy group, an ethylenedioxy group, or a trimethylenedioxy group.

11. The primary phosphine compound according to claim 1, wherein both R$^6$ and R$^7$ pairs are fused together to independently form at least one of a trimethylene group, a tetramethylene group, a pentamethylene group, a methylenedioxy group, an ethylenedioxy group, and a trimethylenedioxy group.

12. The primary phosphine compound according to claim 1, wherein both R$^5$ and R$^6$ pairs are fused together to form methylenedioxy, ethylenedioxy, or trimethylenedioxy groups.

13. The primary phosphine compound according to claim 1, wherein both R$^6$ and R$^7$ pairs are fused together to form methylenedioxy, ethylenedioxy, or trimethylenedioxy groups.

14. The primary phosphine compound according to claim 1, wherein both R$^5$ and R$^6$ pairs are fused together to form a methylenedioxy group.

15. The primary phosphine compound according to claim 1, wherein both R$^6$ and R$^7$ pairs are fused together to form a methylenedioxy group.

16. The primary phosphine compound according to claim 1, wherein both $R^6$ and $R^7$ pairs are fused together to form trimethylene, methylenedioxy, or ethylenedioxy groups.

17. The primary phosphine compound according to claim 1, in the form of an axially asymmetric optically active substance.

18. The primary phosphine compound according to claim 1, in the form of a racemic modification of an axially asymmetric optically active substance.

* * * * *